(12) United States Patent
Brechbiel et al.

(10) Patent No.: US 6,765,104 B1
(45) Date of Patent: Jul. 20, 2004

(54) TRANSITION METAL COMPLEXES OF N, N',N"TRIALKYL-CIS-1,3,5-TRIAMINOCYCLOHEXANE AND RELATED COMPOSITIONS AND METHODS OF SYNTHESIS AND USE

(75) Inventors: Martin Brechbiel, Annadale, VA (US); Roy P. Planalp, Portsmouth, NH (US); Kim Deal, Albany, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 39 days.

(21) Appl. No.: 10/049,115

(22) PCT Filed: Oct. 8, 2000

(86) PCT No.: PCT/US00/21957

§ 371 (c)(1),
(2), (4) Date: Jun. 18, 2002

(87) PCT Pub. No.: WO01/10870

PCT Pub. Date: Feb. 15, 2001

Related U.S. Application Data

(60) Provisional application No. 60/148,051, filed on Aug. 10, 1999.

(51) Int. Cl.[7] .................. C07F 1/08; A61K 55/00; A61B 5/055; C07C 211/00
(52) U.S. Cl. ............. 556/110; 514/499; 424/1.11; 424/1.29; 424/9.3; 424/9.321; 564/462
(58) Field of Search ............ 556/110; 424/1.11, 424/1.29, 9.3, 9.321; 564/462; 514/499

(56) References Cited

U.S. PATENT DOCUMENTS

| 5,281,704 A | 1/1994 | Love et al. ............ 540/465 |
| 5,446,145 A | 8/1995 | Love et al. ............ 540/465 |
| 5,679,810 A | 10/1997 | Love et al. ............ 536/1 |
| 5,739,022 A | 4/1998 | Burstyn et al. ........... 435/184 |

FOREIGN PATENT DOCUMENTS

| JP | 62048859 | 9/1988 |
| JP | 09033631 | 9/1998 |

OTHER PUBLICATIONS

Brand et al., "Zinc complexes of cyclohexas triamine ligands," *Inorganic Chimica Acta*, 198–200, pp. 663–669 (1992).
Deal et al., "Mechanistic Studies of Dichloro(1,4,7–triazacylononane)copper(II)–Catalyzed Phosphate Diester Hydrolysis," *Inorg. Chem.*, 35:10, pp. 2792–2798 (1996).
Hegg et al., "Hydrolysis of Unactivated Peptide Bonds by a Macrocyclic Copper (II) Complex: Cu([9]aneN$_3$)Cl$_2$ Hydrolyzes Both Dipeptides and Proteins," *J. Am. Chem. Soc.*, 117, pp. 7015–7016 (1995).
Hegg et al., "Copper(II) Macrocycles Cleave Single–Stranded and Double–Stranded DNA under Both Aerobic and Anaerobic Conditions," *INorg. Chem.*, 35, pp. 7474–7481 (1996).
Hegg et al., "Hydrolysis of Double–Stranded and Single–Stranded RNA in Hairpin Structures by the Copper(II) Macrocycle Cu([9]aneN$_3$) Cl$_2$," *Inorg. Chem.*, 36, pp. 1715–1718 (1997).
Armanasco et al., *J. Chem. Soc.*, 8:1363–1368 (1997).
Belal et al., *Data. Chemabs 'Online!*, 124:248947 (1994).
Bowen et al., *Bioorg. Med. Chem. Lett.* 6, :807–810 (1996).
Itoh et al. *Chem. Commun.* 1997:677–678 (1997).
Kohn et al., *Chem. Ber.*, 129:1327–1333 (1996).
Kohn et al., *Chem. Ber.*, 129: 25–27 (1996).
Mahapatra, *J. Am. Chem. Soc.*, 116:9785–9786 (1994).
Park, *JBIC* 3:449–457 (1998).
Stetter et al., *Chem. Ber.*106:2523–2529 (1973).

*Primary Examiner*—Porfirio Nazario-Gonzalez
(74) *Attorney, Agent, or Firm*—Leydig, Voit & Mayer, Ltd.

(57) ABSTRACT

The present invention provides transition metal complexes of N,N',N"-trialkyl-cis,cis-1,3,5-triaminocyclohexane and related compositions and methods of synthesis and use in vitro and in vivo, such as a therapeutic agent or a delivery/imaging agent.

35 Claims, 4 Drawing Sheets

TRANSITION METAL COMPLEXES OF N,N',N"TRIALKYL-CIS-1,3,5-TRIAMINOCYCLOHEXANE AND RELATED COMPOSITIONS AND METHODS OF SYNTHESIS AND USE

This application is the U.S. national phase of PCT/US00/21957, which was filed on Aug. 10, 2000, and which claims priority to U.S. provisional application No. 60/148,051, which was filed on Aug. 10, 1999.

TECHNICAL FIELD OF THE INVENTION

The present invention relates to transition metal complexes of N,N',N"-trialkyl-cis,cis-1,3,5-triaminocyclohexane and related compositions and methods of synthesis and use in vitro and in vivo, such as a therapeutic agent or a delivery/imaging agent.

BACKGROUND OF THE INVENTION

Nucleases that hydrolyze phosphate diester bonds exist in nature. Given that phosphate diester bonds are responsible for the accuracy of the genetic code, there has been interest in developing synthetic metallonucleases that hydrolyze phosphate diester bonds (Bashkin, Current Biology 7: R286–R288 (1997); Kuusela et al., Met. Ions Biol. Syst. 32: 271–300 (1996); Morrow, Met. Ions Biol. System. 33: 561–592 (1996); Sigman et al., Chem. Rev. 93: 2295–2361 (1993)). A variety of inert metal compounds have been evaluated as promoters (or catalysts) of activated phosphate diester hydrolysis (Williams et al., J. Am. Chem. Soc. 120: 8079–8087 (1998); Wahnon et al., Chem. Int. Ed. Eng. 34: 2412–2414 (1995); Hendry et al., In Progress in Inorganic Chemistry 38: 201–258, Lippard, ed., John Wiley & Sons, NY (1990); Hendry et al., Inorg. Chem 29: 92–97 (1990); Hendry et al., J. Am. Chem. Soc. 111: 2521–2527 (1989); Chin et al., J. Am. Chem. Soc. 111: 186–190 (1989)). Given that most natural nucleases contain one or two labile metal cations in the active site (Williams, In Comprehensive Biological Catalysts 1: 543–561, Sinnott, ed, Academic Press Ltd., San Diego, Calif. (1998); Cowan, Chem. Rev. 98: 1067–1087 (1998); Strater et al., Angew. Chem. Int. Ed. Engl. 35: 2024–2055 (1996)), recent efforts have focused on labile metal complexes like zinc and copper as synthetic nucleases (Yashiro et al., Chem. Commun. 1997: 83–84; Yashiro et al., J. Chem. Soc. Chem. Commun. 1995: 1793–1794; Gobel, Chem. Int. Ed. Engl. 33: 1141–1143 (1994); Koike et al., J. Am. Chem. Soc. 113: 8935–8941 (1991); de Rosch et al., Inorg. Chem. 29: 2409–2416 (1990); Morrow et al., Inorg. Chem. 27: 3387–3394 (1988)).

Copper (II) complexes have been explored. One of the first systems evaluated was $Cu(2,2'-bipyridine)^{2+}$-catalyzed hydrolysis of ethyl(p-nitrophenyl)phosphate, and rate enhancements were reported (Morrow et al., Inorg. Chem. 27: 3387–3394 (1988)). Since then, others have explored bipyridine and pyridine derivatives as copper (II) ligands (Kovari et al., J. Am. Chem. Soc. 118: 12704–12709 (1996); Kovari et al., J. Chem. Soc. Chem. Commun. 1995: 1205–1206; Young et al., J. Am. Chem. Soc. 117: 9441–9447 (1995)). A variety of activated phosphate diesters and activated transesterification substrates, like bis(2,4-dinitrophenyl)phosphate (Young et al. (1995), supra), bis(p-nitrophenyl)phosphate (Kovari et al. (1996), supra; Kovari et al. (1995), supra), and 2-hydroxypropyl-p-nitrophenyl phosphate (hpnp; Wall et al., Angew. Chem. Int. Ed Engl. 32: 1633–1635 (1993); Wahnon et al., J. Chem. Soc. Chem. Commun. 1994: 1441–1442) have been used to determine the activity of the metal complexes.

Detailed kinetics and mechanistic studies of labile metal-promoted hydrolysis have been reported for the copper (II) triazacyclononane system (Deal et al., Inorg. Chem. 35: 2792–2798 (1996); see, also, Hegg et al., J. Am. Chem. Soc. 117: 7015–7016 (1995); Hegg et al., Inorg. Chem. 35: 7474–7481 (1996); and Hegg et al., Inorg. Chem. 36: 1715–1718 (1997)). Deal and co-workers measured a half-order metal complex dependence attributed to the formation of an inactive di-hydroxide bridged copper(II) dimer in equilibrium with the active mononuclear species (Deal et al. (1996), supra; Fromm, Initial Rate Enzyme Kinetics, Springer-Verlag, NY (1975), pp. 209–213). Studies by others with additional copper (II) complexes also have noted the half-order dependence (Wahnon et al. (1994), supra).

It has been suggested that a dinuclear copper complex which retains open coordination sites on the metal face may better promote phosphate diester hydrolysis (Deal et al., J. Am. Chem. Soc. 118: 1713–1718 (1996)). Wahnon and co-workers (Wahnon et al. (1994), supra) noted that the copper complex of bis(2-benzimidazolylmethyl)amine had an increase in the transesterification rate of hpnp with high metal complex concentrations, which was ascribed to an active dimer. The ligand is bulky, implying that steric constraints placed on the metal complex by the ligand may inhibit dimer formation.

Recently, Itoh and co-workers (Itoh et al., Chem. Commun. 1997: 677–678) reported that the hydrolysis of ethyl (2,4-dinitrophenyl)phosphate by the copper(II) complex of cis,cis-1,3,5-triaminocyclohexane (tach) was significantly greater than that for several other tramino ligands. Until recently, the availability of tach and derivatives thereof was limited by the synthetic procedure.

In view of the above, it is an object of the present invention to provide new synthetic metallonucleases, in particular transition metal complexes of novel derivatives of tach. The novel derivatives of tach enable the formation of complexes with many transition metals and the resultant metallonucleases cleave activated phosphate diesters at an unprecedented rate and demonstrate concentration-dependent cytotoxicity. It is a related object of the present invention to provide a method of synthesizing tach. Such a synthesis route does not suffer from the disadvantages of complexity and low yield associated with currently available methods of synthesis, being less complicated and providing tach in high yield. It is another object of the present invention to provide conjugates of the transition metal complexes of novel derivatives of tach. It is yet another object of the present invention to provide methods of using such complexes and conjugates thereof. These and other objects and advantages of the present invention, as well as additional inventive features, will be apparent from the detailed description provided herein.

BRIEF SUMMARY OF THE INVENTION

The present invention provides a transition metal complex of N,N',N"-trialkyl-cis,cis-1,3,5-triaminocyclohexane. Preferably, the transition metal is copper, in particular copper II (Cu (II)). The trialkyl preferably comprises $C_1$–$C_6$ alkyl groups, which may be the same or different. Preferably, the trialkyl is trimethyl or triethyl, with trimethyl being especially preferred. The transition metal can be radioactive, such as a positron emitter, e.g., $Cu^{64}$, or a β-emitter, e.g, $Cu^{67}$.

The transition metal complex of N,N',N"-trialkyl-cis,cis-1,3,5-triaminocyclohexane can be conjugated to a targeting agent. Preferably, the targeting agent is an immunological agent, a protein, a polypeptide, a peptide, a nucleic acid or a steroid.

Also provided by the present invention is a composition comprising a transition metal complex of N,N',N"-trialkyl-cis,cis-1,3,5-triaminocyclohexane, or a conjugate thereof, and a carrier therefor.

In addition to the above, the present invention provides a method of synthesizing N,N',N"-trialkyl-cis,cis-1,3,5-triaminocyclohexane. The method comprises derivatizing 1,3,5-cis,cis-triaminocyclohexane to a tris-sulfonamide, removing the sulfonamide proton with a base to generate a tris-anion, quenching the tris-anion with an alkylating agent, and cleaving the sulfonamide group with an acid to generate N,N',N"-trialkyl-cis,cis-1,3,5-triaminocyclohexane as a protonated salt. The method can further comprise adding an equimolar amount of $CuX_2$ in water to the N,N',N"-trialkyl-cis,cis-1,3,5-triaminocyclohexane, neutralizing the resulting solution with base solution (to form a deep-blue solution), and removing the hydroxides that form by filtration to yield a solution of the Cu (II) complex.

Further provided by the present invention is a method of cleaving a biological molecule. The method comprises contacting the biological molecule with an above-described complex, which cleaves the biological molecule. Preferably, the biological molecule is in vivo and the cleavage of the biological molecule has a therapeutic effect. Also preferably, the complex is targeted to an abnormally proliferating cell that comprises the biological molecule, such as a cancerous cell and the therapeutic effect is the treatment of cancer.

Still further provided by the present invention is a method of inhibiting expression of a nucleic acid. The method comprises contacting a nucleic acid with an above-described transition metal complex conjugated to an antisense nucleic acid specific for the nucleic acid, whereupon the antisense nucleic acid binds to the nucleic acid, thereby inhibiting expression of the nucleic acid.

In another embodiment, the present invention provides a method of radiation therapy. The method comprises administering to an animal in need of radiation therapy a therapeutically effective amount of an above-described radioactive complex, which is (i) conjugated to a targeting agent that binds to a molecule on the surface of a cell to be treated with radiation or (ii) encapsulated in a liposome comprising on its surface the targeting agent.

In yet another embodiment, a method of imaging is provided. The method comprises (i) administering to an animal an imaging effective amount of an above-described radioactive complex, which is either conjugated to a targeting agent that binds to a molecule on the surface of a cell to be imaged or encapsulated in a liposome comprising on its surface the targeting agent, and (ii) imaging the complex. Preferably, the targeting agent is an immunological agent.

In still yet another embodiment, the present invention provides a method of tracing a compound in an animal. The method comprises administering to an animal a mixture of the compound and an above-described complex and tracing the location of the complex in the animal.

DETAILED DESCRIPTION OF THE INVENTION

Figure 1:
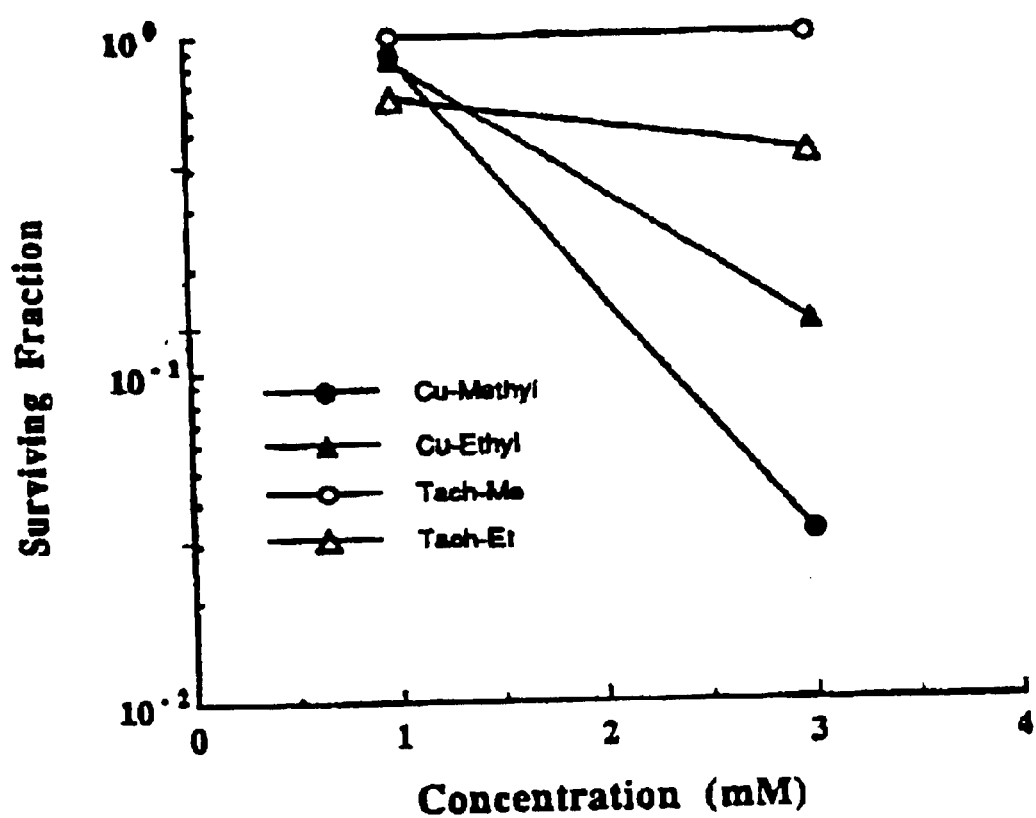
FIG. 1 is a graph of the cytotoxicity of an N,N',N"-trialkyl-cis,cis-1,3,5-triaminocyclohexane complexed with copper, or alone, as measured by the surviving fraction of cells as a function of the concentration of the N,N',N"-trialkyl-cis,cis-1,3,5-triaminocyclohexane (mM).

The present invention is predicated on the surprising and unexpected discovery of transition metal complexes of N,N',N"-trialkyl-cis,cis-1,3,5-triaminocyclohexane, which can cleave activated phosphate diesters at an unprecedented rate and demonstrate concentration-dependent cytotoxicity. The present invention is also predicated on the discovery of a method of synthesizing tri-alkyl-cis,cis-1,3,5-triaminocyclohexane, which is less complicated and provides higher yields than currently available methods of synthesis.

In view of the above, the present invention provides in one embodiment transition metal complexes of N,N',N"-trialkyl-cis,cis-1,3,5-triaminocyclohexane. Preferably, the transition metal is copper, in particular copper II. The trialkyl preferably comprises $C_1$–$C_6$ alkyl groups, which may be the same or different Trimethyl and triethyl are preferred as the trialkyl, with trimethyl being especially preferred.

In one embodiment of the transition metal complexes of N,N',N"-trialkyl-cis,cis-1,3,5-triaminocyclohexane, the transition metal is preferably radioactive. A preferred radioactive transition metal is a positron emitter, such as $Cu^{64}$. Another preferred radioactive transition metal is a $\beta$-emitter, such as $Cu^{67}$.

While N,N',N"-trialkyl-cis,cis-1,3,5-triaminocyclohexane can be synthesized in accordance with methods known in the art (Stetter et al., Chem. Ber. 106: 2523–2529 (1973)), preferably N,N',N"-trialkyl-cis,cis-1,3,5-triaminocyclohexane and transition metal complexes thereof are synthesized in accordance with the methods set forth herein.

The above-described complex can be conjugated to a targeting agent. By "targeting agent" is meant any means that enables specific interaction with a target The targeting agent can bind to a defined population of cells through a receptor, a substrate, an antigenic determinant or another binding site on the target cell population. Examples include an "immunological agent," which is used herein to refer to an antibody, such as a polyclonal antibody or a monoclonal antibody, an immunologically reactive fragment of an antibody, an engineered immunoprotein and the like; a protein (target is receptor, as substrate, or regulatory site on DNA or RNA); a polypeptide; a peptide (target is receptor); a nucleic acid, which is DNA or RNA, single-stranded or double-stranded, synthetic or isolated and purified from nature (target is complementary nucleic acid); a steroid (target is steroid receptor); and the like. Preferred targeting agents include an antibody or an immunologically reactive fragment thereof, a peptide, e.g., bombesin, gastrin-releasing peptide, RGD peptide, substance P, neuromedin-B, neuromedin-C, somatostatin, octreotide analogues, and metenkephalin, and a hormone, e.g., estradiol, neurotensin, melanocyte stimulating hormone, follicle analogues stimulating hormone, leutenizing hormone, and human growth hormone. Other suitable targeting agents include serum proteins, fibrinolytic enzymes, and biological response modifiers, such as interleukin, interferon, erythropoietin, and colony-stimulating factor. Analogs of targeting agents that retain the ability to bind to a defined target also can be used. In addition, synthetic targeting agents can be designed, such as to fit a particular epitope. The targeting agent can include any linking group that can be used to join a targeting agent to, in the context of the present invention, a complex. It will be evident to one skilled in the art that a variety of linking groups, including bifunctional reagents, can be used.

An above-described complex can be conjugated to a targeting agent by covalent or non-covalent bonding. If bonding is non-covalent, the conjugation can be through hydrogen bonding, ionic bonding, hydrophobic or van der Waals interactions, or any other appropriate type of binding.

In view of the above, the present invention provides in another embodiment a composition, e.g., a pharmaceutical composition, comprising an above-described complex, or conjugate thereof, and a carrier therefor, e.g., a pharmaceutically acceptable carrier. Suitable carriers for in vitro and in vivo use are known in the art. A biologically acceptable, normal saline solution can be appropriately employed. The carrier can include a minor amount of a carrier protein, such as human serum albumin, for example, to stabilize the targeting agent. Stabilizers, antioxidants, osmolality adjusting agents, buffers, pH adjusting agents, etc., can be included in the composition. The composition can be in the form of a solution, suspension or dispersion. Suitable additives include, for example, physiologically biocompatible buffers, additions of chelants or calcium chelate complexes, or optionally, additions of calcium or sodium salts.

Parenterally administrable forms, e.g., intravenous forms, should be sterile and free from physiologically unacceptable agents and should have low osmolality to minimize irritation or other adverse effects upon administration. Suitable vehicles include aqueous vehicles customarily used for administering parenteral solutions, such as sodium chloride injection, Ringer's injection, and dextrose injection. Lactated Ringer's injection and other solutions are as described in *Remington's Pharmaceutical Sciences*, 15th ed., Easton: Mack Publishing Co. (1975). The solutions can contain preservatives, antimicrobial agents, buffers and antioxidants conventionally used for parenteral solutions and excipients and other additives that are compatible with the chelates and will not interfere with the manufacture, storage or use of products.

The concentration of complex or conjugate thereof in a composition will be a matter of choice. Levels of 0.5 mg/ml are readily attainable but the concentration may vary considerably depending upon the specifics of any given application. Appropriate concentrations of biologically active materials in a carrier are routinely determined in the art.

The effective dose of complex or conjugate thereof to be utilized for any application will also depend upon the particulars of that application. In treating tumors in the context of radioinmmunotherapy, for example, the dose will depend, inter alia, upon tumor burden, accessibility, route of administration, administration of other active agents, and the like. Generally, a therapeutically effective dose is from about 20 mCi to about 300 mCi.

The complexes and conjugates thereof can be administered in accordance with the present inventive methods by any suitable route. Such routes include intravenous, intraperitoneal, and the like, depending on the disease or cancer to be treated, respectively, the location of the diseased/cancerous cells, the extent of disease/cancer, and other factors. The determination of the appropriate route(s) of administration for a given application is within the skill in the art.

The present invention provides as another embodiment a method of synthesizing N,N',N"-trialkyl-cis,cis-1,3,5-triaminocyclohexane. The method comprises the derivatization of 1,3,5-cis,cis-triaminocyclohexane to a tris-sulfonamide. The sulfonamide proton is then removed by a base (e.g., NaH) to generate the tris-anion. The tris-anion is then quenched with an alkylating agent (e.g., a dialkylsulphonate, although alkyl halides are not excluded). The sulfonamide group is then cleaved with an acid to generate the N,N',N"-trialkyl-cis,cis-1,3,5-triaminocyclohexane as a protonated salt The method can further comprise the addition of an equimolar amount of $CuX_2$ in water to the N,N',N"-trialkyl-cis,cis1,3,5-triaminocyclohexane, which is then neutralized with base, e.g., 3 equivalents,to form a deep-blue solution. The hydroxides that form are removed by filtration to yield a solution of the Cu (II) complex.

In still yet another embodiment of the present invention, a method of cleaving a biological molecule is provided. The biological molecule comprises a peptide linkage or a phosphodiester bond and, thus, is preferably a peptide, polypeptide, protein or nucleic acid. The method comprises contacting a biological molecule with an above-described complex, whereupon the complex cleaves the biological molecule. Preferably, the biological molecule is in vivo and the cleavage of the biological molecule has a therapeutic effect, such as the treatment of disease, in particular a disease associated with abnormal cellular proliferation, such as cancer. Also preferably, the complex is targeted to an abnormally proliferating cell, which comprises the biological molecule to be cleaved. In this regard, the abnormally proliferating cell is preferably a cancerous cell and the therapeutic effect is the treatment of cancer.

It is also expected that the complex is advantageously suitable for cleavage of other agents having phosphodiester linkages or derivatives thereof, e.g., anticholinesterases, such as insecticides having oxygen-phosphorus linkages (see, generally, U.S. Pat. No. 5,739,022 (Burstyn et al.)).

The complex can be targeted to an abnormally proliferating cell, such as a cancerous cell, by conjugation to a targeting agent that binds to a molecule on the surface of the abnormally proliferating cell. Preferably, the targeting agent is an immunological agent, which can be generated in accordance with methods known in the art (see, generally, Pietersz et al., *Adv. Exp. Med. Biol.* 353: 169–179 (1994); Riethmuller et al., *Cur. Opin. Immuno.* 5: 732–739 (1993); Senter, *FASEB J.* 4: 188–193 (1990)). Examples of cell-surface molecules that can be targeted by the immunological agent include CD-20 in non-Hodgkins B-cell lymphoma, CD-33 in myelogenous leukemia, and the IL-2 receptor that is up-regulated in T-cell diseases, such as adult T-cell leukemia.

The complex also can be targeted to an abnormally proliferating cell, such as a cancerous cell, by encapsulation in a liposome comprising on its surface a targeting agent that binds to a molecule on the surface of the abnormally proliferating cell. When the complex is encapsulated in a liposome, the complex can be conjugated to an antisense nucleic acid that binds to a sense nucleic acid, which is expressed in an abnormally proliferating cell but not in a normally proliferating cell or which is expressed in an abnormally proliferating cell at a higher level than in a normally proliferating cell, whereupon expression of the sense nucleic acid is inhibited. The antisense nucleic acid can further comprise a ribozyme sequence.

Alternatively, the complex can be targeted to an abnormally proliferating cell, such as a cancerous cell, by direct administration to the abnormally proliferating cell. For example, when the abnormally proliferating cell is a tumor cell, the complex can be administered intratumorally or peritumorally, such as by injection.

The present inventive method can be used to treat any suitable cancer alone or in combination with any suitable anti-cancer therapy. Suitable cancers include cancers of the brain, lung (e.g., small cell and non-small cell), ovary, breast, prostate, and colon, as well as other carcinomas and sarcomas. A suitable anti-cancer therapy may include radiation and/or drug therapy, which includes those drugs given in treatment of the various conditions described above, examples of which can be found in the Physicians' Desk Reference (1998).

In the context of the method of cleaving a biological molecule in vivo, when the complex comprises a radioactive transition metal, such as radioactive copper, the radioactive copper is preferably cytotoxic to the abnormally proliferating cell. Cytotoxicity can be concentration-dependent. The determination of a cytotoxic concentration is a matter of routine experimentation, using methods known in the art.

A further embodiment of the present invention is a method of inhibiting expression of a nucleic acid. The method comprises contacting the nucleic acid with an above-described complex conjugated to an antisense nucleic acid specific for the nucleic acid to be inhibited. The antisense nucleic acid can further comprise a ribozyme sequence. The antisense nucleic acid binds to the nucleic acid, thereby inhibiting its expression (see, e.g., Senior, *Bioteck Genet. Eng. Rev.* 15: 79–119 (1998); Bird et al., *Biotech. Genet. Eng. Rev.* 9: 207–227(1991); Matzke et al., *Trends Genet.* 11(1): 1–3 (1995); Baulcombe, *Plant Mol. Biol.* 32(1–2): 79–88 (1996); Cstanatto et al., *Crit. Rev. Eukaryot. Gene Exp.* 2(4): 331–357 (1992); and Rossi, *Trends Biotechnol.* 13(8): 301–306 (1995)).

Antisense nucleic acids can be generated in accordance with methods known in the art. The nucleic acid sequence introduced in antisense inhibition generally is substantially identical to at least a portion, preferably at least about 20 continuous nucleotides, of the nucleic acid to be inhibited, but need not be identical. The complex can, thus, be designed such that the inhibitory effect applies to other proteins within a family of genes exhibiting homology or substantial homology to the nucleic acid. The introduced sequence also need not be full-length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988). Preferably, the ribozyme comprises at least about 20 continuous nucleotides complementary to the target sequence on each side of the active site of the ribozyme.

A still further embodiment of the present invention is a method of radiation therapy. The method comprises administering to an animal in need of radiation therapy a therapeutically effective amount of an above-described complex. The complex can be (i) conjugated to a targeting agent that binds to a molecule on the surface of a cell to be treated with radiation or (ii) encapsulated in a liposome comprising on its surface the targeting agent. What constitutes a therapeutically effective amount can be determined in accordance with methods known in the art. The targeting agent preferably is an immunological agent.

A method of imaging is also provided by the present invention. The method comprises administering to an animal an imaging effective amount of an above-described complex and imaging the complex. The complex can be (i) conjugated to a targeting agent that binds to a molecule on the surface of a cell to be imaged or (ii) encapsulated in a liposome comprising on its surface the targeting agent. An imaging effective amount also can be determined in accordance with methods known in the art. The targeting agent preferably is an immunological agent. Imaging means are also known in the art and include positive emission tomography (PET), which is a highly specialized research imaging technique using short-lived radioactive substances, usually those made with a cyclotron, single photon emission computed tomography (SPECT), and gamma-camera scintigraphy, which produces photographs or cathode-ray tube images of the gamma-ray emissions from organs containing radionuclide tracers.

Further provided is a method of tracing a compound in an animal. The method comprises administering to the animal a mixture of the compound and an above-described complex and tracing the location of the complex in the animal. The location of the complex indicates the location of the compound. Methods of tracing a compound is this manner are known in the art and include determination by PET, SPECT, scintigraphic imaging and detailed necroscopy biodistribution methods of intrinsically radiolabelling complexes (using either tritium or $C^{14}$).

The complexes and conjugates of the present invention also have other uses. Such uses include drug design, the study of the role of transition metal ions, in particular copper ions, in enzyme catalysis, and the study of gene expression.

EXAMPLES

The following examples serve to illustrate the present invention and are not intended to limit its scope in any way.

Anhydrous grade methanol was obtained from Fisher Scientific (Pittsburg, Pa.). Ethanol was distilled from sodium/potassium Anhydrous grade dimethylsufoxide (DMSO) and dimethylformamide (DMF) were obtained from Aldrich (Milwaukee, Wiss.). Dipropyl sulfate was purchased from TCI America (Portland, Oreg.). N,N',N"-cis,cis-triaminocyclohexane trihydrobromide, ,N',N"-trimethyl or triethyl-cis,cis-1,3,5-triaminocyclohexane were synthesized as previously reported (Bowen et al., *Bioorg. Med. Chem. Lett.* 6: 807–810 (1996); Park, *JBIC* 3: 449–457 (1998)). The buffer HEPES (N-(2-hydroxyethyl)piperazine-N'-ethanesulfonic acid), MES (N-morpholineethanesulfonic acid), EPPS (N-(2-hydroxyethyl)piperazine-N'-propanesulfonic acid) and CHES (2-(N-cyclohexylamino) ethanesulfonic acid) were purchased from Sigma Chemical Co (St. Louis, Mo.). Sodium bis(4-nitrophenyl)phosphate, disodium 4-nitrophenyl phosphate, copper chloride, triethylamine and sodium perchlorate were purchased from Aldrich. Sodium hydroxide and acetic acid were purchased from Mallinckrodt Chemical Co. (Paris, Ky.). HPLC grade methanol was purchased from J. T. Baker (Phillipsburg, N.J.). Other reagents were from Aldrich, Sigma Chemical Co. or Fluka (Ronkonkoma, N.Y.). Triethylamine was distilled from calcium hydride before use, and all other chemicals were used without further purification. Aqueous solutions were prepared with water purified by passage through a Hydro ultrapure water filtration system.

An Accumet pH meter 925 equipped with an Orion 8103 Ross semi-micro combination pH electrode was used for pH measurements. Kinetic measurements were performed on a Hewlett-Packard Diode Array UV/V is Spectrometer 845 A with a water jacketed multicell holder interfaced with an IBM PC. The temperature of the multicell holder was maintained with a Form Scientific circulating bath. Quartz cuvettes with threaded caps were obtained from Hellma HPLC analysis was performed on a Beckman system with a variable wavelength detector interfaced with a PC. Separations were obtained on a Beckman ODS reverse phase column (4.6 mm×25 cm).

$^1$H and $^{13}$C NMR were obtained using a Varian Gemini 300 instrument or at 360 MHz with a Bruker AM360 instrument. Chemical shifts are reported in ppm on the δ scale relative to TMS, TSP or solvent Proton chemical shifts are annotated as follows: ppm (multiplicity, integral, coupling constant (Hz)). Chemical ionization mass spectra (CI-MS) were obtained on a Finnegan 3000 instrument. Fast atom bombardment (FAB-MS) mass spectra were taken on an Extrel 400. Elemental analysis was performed by Atlantic Microlabs (Atlanta, Ga.) or by Galbraith Laboratories (Knoxville, Tenn.).

Example 1

This example describes the synthesis of the copper complex of N,N',N"-trimethyl-cis,cis-1,3,5-triaminocyclohexane.

A mixture of N,N',N"-trimethyl-cis,cis-1,3,5-triaminocyclohexane.3HBr (prepared as described previously in Bowen et al. (1996)) (0.12 g, $2.9 \times 10^{-4}$ mol) in water (5 ml), $Na_2CO_3 \cdot H_2O$ (0.054 g, $4.4 \times 10^{-4}$ mol, 1.5 equiv) in water (5 ml), and benzene (100 ml) was stirred and heated in a 250 ml round-bottomed flask fitted with a Dean-Stark trap with a water-cooled condenser. Benzene-water azeotrope was distilled for 14 hr with collection of around 11.7 ml of water. The benzene layer was transferred to another 250 ml round-bottomed flask and dried under reduced pressure to give N,N',N"-trimethyl-cis,cis-1,3,5-triaminocyclohexane as a white solid. The solid was dissolved in a mixture of chloroform (2 ml) and diethylether (4 ml) and added to a green solution of $CuCl_2$ (0.040 g, $2.9 \times 10^{-4}$ mol) in a mixture of methanol/ethanol (2 ml/4 ml) affording a green precipitate immediately. Decanting the supernatant and extracting the solid with $CH_2Cl_2$ (5 ml) followed by drying under reduced pressure afforded the product as a green solid. (0.056 g, $1.8 \times 10^{-4}$ mol, 63%) Anal. Calc. For $C_9H21N_3CuCl_2$: C, 35.36; H, 6.92; N, 13.74. Found: C, 35.16; H, 6.85; N, 13.62. UV (methanol) 675 nm ($\epsilon$=119.1). MS (FAB/DMSO/glycerol): 234 (M-$Cl_2$)

The same method can be used to synthesize the copper complex of N,N',N"-triethyl-cis,cis-1,3,5-triaminocyclohexane using N,N',N"-triethyl-cis,cis-1,3,5-triaminocyclohexane.3HBr as the starting material.

Example 2

This example describes the preparation of the copper (II) complex of N,N',N"-triethyl-cis,cis-1,3,5-triaminocyclohexane in situ.

N,N',N"-trimethyl-cis,cis-1,3,5-triaminocyclohexane.3 HBr was prepared as described previously (Park (1998)). The copper (II) complex was generated in situ by adding 1.49 ml of 0.1M $CuCl_2$ in water to 1.5 ml of 0.1 M of N,N',N'-trimethyl-cis,cis-1,3,5-triaminocyclohexane, neutralized with three equivalents of sodium hydroxide, in water. A deep blue solution formed immediately and was used without further purification. Occasionally, a faint blue-green precipitate formed, presumably insoluble copper (II) hydroxides, which was removed by filtration through a 0.22 $\mu$m syringe filter.

Example 3

This example demonstrates the activity of the copper (II) complex of N,N',N"-trimethyl-cis,cis-1,3,5-triaminocyclohexane.

The copper (II) complex of N,N',N"-trimethyl-cis,cis-1,3,5-triaminocyclohexane prepared in accordance with the method of Example 2 (1 mM) was combined with bis(4-nitrophenyl)phosphate (1 mM) and HEPES (50 mM), pH 7.24, at 50° C. and incubated, while monitoring for an increase in absorbance at 400 nm. An aliquot was withdrawn and analyzed by reverse phase HPLC, eluted with a linear gradient of 100% 50 mM acetic acid/50 mM triethylamine to 100% methanol over thirty minutes. The signals observed in the reaction mixture corresponded to the predicted hydrolytic products, p-nitrophenyl phosphate (10.5 min) and 4-nitrophenolate (16.8 min), as well as unreacted bis(p-nitrophenyl)phosphate (20.2 min). Products were confirmed by co-injection of standards. No other UV active peaks were observed, indicating that the reaction was hydrolytic.

Measurements were performed as previously described (Deal et al. (*Inorg. Chem.* 1996), supra). Briefly, the initial rate of formation of 4-nitrophenolate was monitored spectrophotometrically at 400 nm for 1 hr or for less than 10% conversion of bis(p-nitrophenyl)phosphate to products. Reactions were run in sets of four, triplicate reaction mixtures and one reference. Spontaneous hydrolysis of the phosphate diester was corrected in the reference, which was identical to the reaction mixture, except lacking metal complex. The concentration of 4-nitrophenolate was calculated from the absorbance using an extinction coefficient of 18700 L $mol^{-1}$ $cm^{-1}$. The initial rate was obtained from the slope of the plots of 4-nitrophenolate concentration vs. time.

Excess copper (II) resulted in the precipitation of copper (II) as hydroxide salts; accordingly, the greatest hydrolytic rate was obtained with equal concentrations of copper (II) and N,N',N"-trimethyl-cis,cis-1,3,5-triaminocyclohexane. In addition, the hydrolysis of bis(p-nitrophenyl)phosphate by the copper (II) complex of N,N',N"-trimethyl-cis,cis-1, 3,5-triaminocyclohexane was metal-dependent The initial rate of hydrolysis showed second-order dependence with respect to the metal complex. A plot of the initial rate versus the concentration of the copper (II) complex of N,N',N"-trimethyl-cis,cis-1,3,5-triaminocyclohexane squared was linear with a slope of $9 \times 10-5$ $Ms^{-1}$ (R=0.996).

Initially first order, the hydrolysis of bis(p-nitrophenyl) phosphate was easily saturated at high concentration relative to the copper (II) complex of N,N',N"-trimethyl-cis,cis-1,3, 5-triaminocyclohexane. The system was easily saturated, indicating that the metal complex has a relatively high affinity for the substrate. The behavior could be fit to a modified Lineweaver-Burke function. Analysis yielded a Michaelis Constant ($K_m$) of 4.4 mM and a maximal velocity ($V_{max}$) of $9.3 \times 10^{-8}$ $s^{-1}$. The initial rate of hydrolysis increased with increasing pH, and no pH-independent region was observed up to pH 9.5. A plot of the log initial rate versus pH yielded a curve that could be analyzed by the Dixon method. The computer generated fit of the curve resulted in a pKa of 7.3, consistent with the deprotonation of a copper(II) coordinated water molecule. Deprotonation of the second water molecule was not observed. The hydrolysis of bis(p-nitrophenyl)phosphate by the copper (II) complex of N,N',N"-trimethyl-cis,cis-1,3,5-triaminocyclohexane could be inhibited by p-nitrophenylphosphate produced in the reaction and by other chelating anions. The greatest inhibition was observed with pyrophosphate. The hydrolysis reaction was completely inhibited with the addition of 0.5 equivalents of pyrophosphate relative to the copper complex. Phosphate was also a potent inhibitor. As the concentration of phosphate was increased, a dramatic drop in linearity of the kinetics and a faint precipitate was observed, indicating precipitation of the copper complex as a phosphate complex. Phenyl phosphate proved to be a better inhibitor than p-nitrophenyl phosphate.

Bis(p-nitrophenyl)phosphate was hydrolyzed more rapidly than ethyl (p-nitrophenyl)phosphate, which was hydrolyzed more rapidly than p-nitrophenyl phosphate. Thus, the rate of metal-promoted hydrolysis is dependent on the electron-withdrawing ability of the leaving group. Leaving groups which are strongly electron-withdrawing are considered activated and hydrolyze more rapidly.

The rate of phosphate diester hydrolysis promoted by the copper (II) complex of N,N',N"-trimethyl-cis,cis-1,3,5-triaminocyclohexane was approximately 6.5 times faster than the rate ($1.3 \times 10^{-6}$ s$^{-1}$; Deal et al. (*Inorg. Chem.* 1996), supra) of phosphate diester hydrolysis promoted by the copper (II) triazacyclononane system. A similar rate acceleration of 6.7 was observed for ethyl (p-nitrophenyl) phosphate by the copper (II) complex of N,N',N"-trimethyl-cis,cis-1,3,5-triaminocyclohexane as compared to the copper (II) triazacyclononane system ($k_{obs}$=$7.2 \times 10^{-8}$s$^{-1}$). Comparable accelerations were observed for bis(p-nitrophenyl)phosphate and ethyl (p-nitrophenyl)phosphate.

Saturation kinetic studies indicated that the copper (II) complex of N,N',N"-trimethyl-cis,cis-1,3,5-triaminocyclohexane was saturated at relatively low concentrations of bis(p-nitrophenyl)phosphate. Such results are in distinct contrast to the copper (II) triazacyclononane system.

Example 4

This example demonstrates the cytotoxicity of the copper complex of N;N',N"-trialkyl-cis,cis-1,3,5-triaminocyclohexane in vitro as determined by the surviving fraction of cells after incubation with varying concentrations of trimethyl and triethyl copper complexes for 1 hr or 24 hrs.

Chinese hamster V79 cells were maintained in a 5% CO$_2$/95% air humidified atmosphere at 37° C. in nutrient mixture F12 with 10% heat-inactivated fetal bovine serum and antibiotics. One day before each experiment, $5 \times 10^5$ V79 cells were plated into 100 mm petri dishes and incubated overnight The cells were exposed to the copper complex of N,N',N"-triethyl-cis,cis-1,3,5-triaminocyclohexane or N,N, N"-triethyl-cis,cis-1,3,5-triaminocyclohexane or the corresponding ligand of N,N',N"-triethyl-cis,cis-1,3,5-triaminocyclohexane or N,N',N"-triethyl-cis,cis-1,3,5-triaminocyclohexane alone for 1 or 24 hours, after which they were rinsed, trypsinized, and plated for macroscopic colony formation. After incubating for 7 days, colonies were fixed with methanol/acetic acid and stained with crystal violet. Colonies larger than 50 cells were counted.

Results are shown in FIG. 1, which is a graph of the cytotoxicity of the N,',N"-trialkyl-cis,cis-1,3,5-triaminocyclohexane copper complex as measured by the surviving fraction of V79 cells as a function of the concentration of the copper complex (mM). A copper complex containing a trimethyl as the trialkyl, at a concentration of 3 mM, is sufficiently cytotoxic that 3% of the treated cells survive. Also cytotoxic is a copper complex containing a triethyl group as the trialkyl; at a concentration of 3 mM, 15% of the treated cells survive. In contrast, when the N,N',N"-trialkyl-cis,cis-1,3,5-triaminocyclohexane is not complexed with copper, 40%/–90% of the treated cells survive at a concentration of 3 mM. The cytotoxicity of the N,N',N"-trialkyl-cis,cis-1,3,5-triaminocyclohexane copper complex increases steadily as a function of the concentration administered regardless of whether the trialkyl is trimethyl or triethyl.

Figure 2:
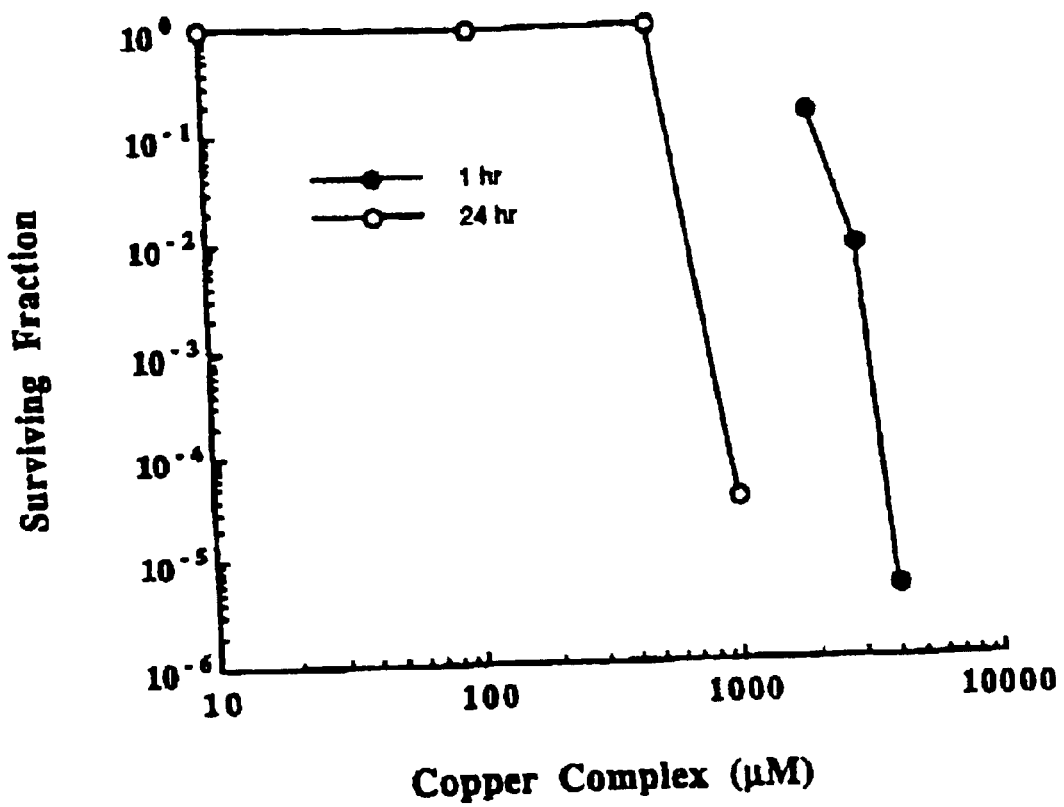
FIG. 2 is a graph of the cytotoxicity of an N,N',N"-trimethyl-cis,cis-1,3,5-triaminocyclohexane copper complex after 1 hr and 24 hrs as measured by the surviving fraction of cells as a function of the concentration of the N,N',N"-trimethyl-cis,cis-1,3,5-triaminocyclohexane copper complex ($\mu$M).

Results after incubation for 1 hour as compared to incubation for 24 hours are shown in FIG. 2, which is a graph of the cytotoxicity of the N,N',N"-trimethyl-cis,cis-1,3,5-triaminocyclohexane copper complex after 1 hr and 24 hrs as measured by the surviving fraction of V79 cells as a function of the concentration of the copper complex ($\mu$M). 1000 $\mu$M of the copper complex produces approximately the same effect when the cells are treated for 24 hrs with the copper complex as when the cells are treated with 4000 $\mu$M of the copper complex for 1 hr. Therefore, less N,N',N"-triethyl-cis,cis-1,3,5-triaminocyclohexane copper complex is need to produce the same result when the cells are treated with the complex for 24 hrs as opposed to 1 hr.

This example demonstrates that the copper complex of N,N',N"-trialkyl-cis,cis-1,3,5-triaminocyclohexane is cytotoxic to cells in vitro. Cytotoxicity of the copper complex is a result of the contact between the copper complex and a biomolecule of the cell. Upon contact with the biomolecule, the copper complex cleaves the biomolecule, namely through cleavage of a peptide bond or phosphodiester linkage within the biomolecule. As cell survival is directly dependent upon intactness of its biomolecules, upon cleavage, the cell is not longer viable. Therefore, this example also implicitly demonstrates cleavage of a biomolecule with the copper complex of N,N',N"-trimethyl-cis,cis-1,3,5-triaminocyclohexane.

Example 5

This example demonstrates the cytotoxicity of a copper complex of N,N',N"-trimethyl-cis,cis-1,3,5-triaminocyclohexane in vitro to cells under tumor-type conditions. Often the interior of a solid tumor is hypoxic because the vascular network necessary to supply the needed oxygen to the tumor cells is not sufficiently developed. Often hypoxic conditions create a situation where the cells are highly resistant to radiation or drug therapy. In this experiment, induced hypoxia was used to mimic the conditions found in the interior of a solid tumor. This example also demonstrates the cytotoxicity of a copper complex of N,N', N"-trimethyl-cis,cis-1,3,5-triaminocyclohexane in combination with radiation therapy.

MCF-7 human mammary carcinoma cells were maintained in a 5% CO$_2$/95% air humidified atmosphere at 37° C. in RPMI 1640 with 10% heat-inactivated fetal bovine serum and antibiotics.

For hypoxia experiments, $3 \times 10^5$ MCF-7 cells were plated into glass flasks, and incubated overnight The flasks were sealed with a rubber stopper, and two hypodermic needles were inserted to allow for gassing. Flasks were gassed with a 95% nitrogen/5% carbon dioxide mixture for one hour. The copper complex was added to the cells after they were hypoxic through a glass sidearm connected to the flask by a ground glass connection. Cells were incubated for 1 hour for experiments to assess the toxicity of the copper complex, then plated and incubated as described previously in Example 4.

Figure 3:
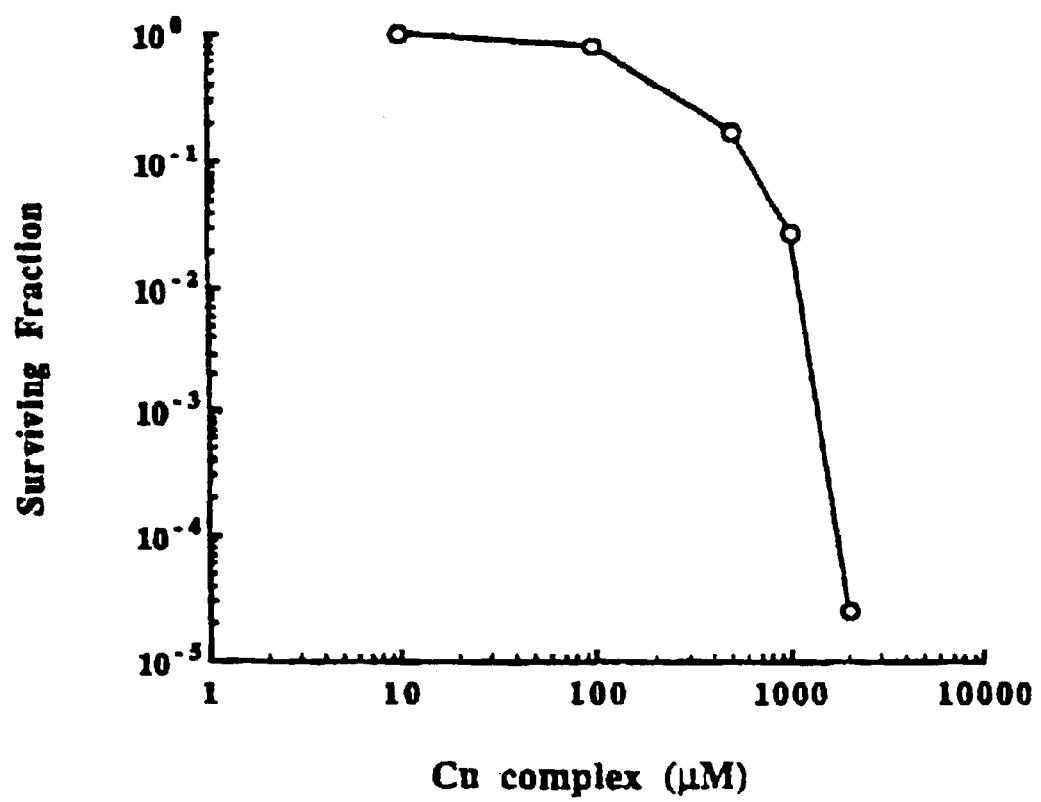
FIG. 3 is a graph of the cytotoxicity of an N,N',N"-trimethyl-cis,cis-1,3,5-triaminocyclohexane copper complex as measured by the surviving fraction of hypoxic cells as a function of the concentration of the N,N',N"-trimethyl-cis,cis-1,3,5-triaminocyclohexane copper complex ($\mu$M).

FIG. 3, which is a graph of the cytotoxicity of the copper complex as measured by the surviving fraction of hypoxic MCF-7 cells as a function of the concentration of the copper complex EM), shows that at a concentration of 1500 $\mu$M, the copper complex destroyed approximately 99% of the treated hypoxic cells.

For hypoxic irradiation experiments, cells were incubated with the copper complex for 15 minutes, then irradiated, plated and incubated as described previously in Example 4. Cells were irradiated with an Eldorado 8 Cobalt-60 teletherapy machine (Theratronics International Ltd., Kanata, Ontario, Canada). The dose rate varied form 200 to 150 cGy/min during the course of this study. Decay corrections were done monthly, and full electron equilibrium was ensured for all irradiations.

Figure 4:
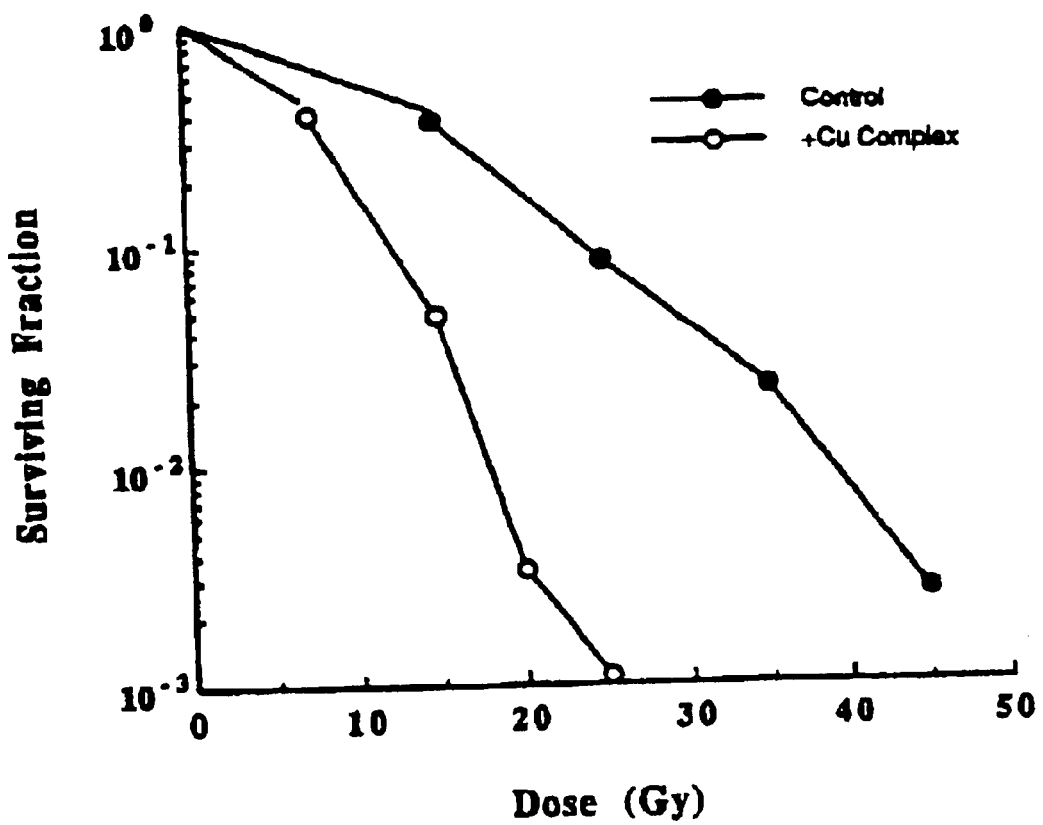
FIG. 4 is a graph of the cytotoxicity of radiation treatment in combination with an N,N',N"-trimethyl-cis,cis-1,3,5-triaminocyclohexane copper complex as measured by the surviving fraction of hypoxic cells as a function of the dose of radiation (Gy) administered to the hypoxic cells.

Approximately twice the amount of radiation alone is needed to produce the same effect on hypoxic cells as radiation plus the N,N',N"-trimethyl-cis,cis-1,3,5-triaminocyclohexane copper complex, as shown in FIG. 4, which is a graph of the cytotoxicity of radiation treatment in combination with the copper complex as measured by the surviving fraction of hypoxic MCF-7 cells as a function of the dose of radiation (Gy) administered to the cells.

This example demonstrates the cytotoxicity of the copper complex of N,N',N"-trimethyl-cis,cis-1,3,5-triaminocyclohexane to abnormally proliferating cells as a treatment for cancer (i.e., under tumor-type conditions). In addition, this example demonstrates the efficacy of the treatment of cancer (i.e., under tumor-type conditions) with the copper complex of N,N',N''-trimethyl-cis,cis-1,3,5-triaminocyclohexane in combination with a traditional method of cancer therapy, e.g., radiation therapy.

The documents cited herein (e.g., patents, patent applications and journal articles) are hereby incorporated in their entireties by reference.

While the present invention has been described with an emphasis upon preferred embodiments, it will be obvious to those of ordinary skill in the art that the present invention can be practiced other than as specifically described herein. Accordingly, the present invention includes all modifications encompassed within the spirit and scope of the invention as defined by the following claims.

What is claimed is:

1. A copper complex of N,N',N''-trialkyl-cis,cis-1,3,5-triaminocyclohexane.

2. The complex of claim 1, wherein said trialkyl contains $C_1$—$C_6$ alkyl groups, which may be the same or different.

3. The complex of claim 2, wherein said trialkyl is trimethyl.

4. The complex of claim 2, wherein said trialkyl is triethyl.

5. The complex of claim 1, wherein said copper is copper II.

6. The complex of claim 1, wherein the copper is radioactive.

7. The complex of claim 6, wherein the copper is a positron emitter.

8. The complex of claim 7, wherein said positron emitter is $Cu^{64}$.

9. The complex of claim 6, wherein the copper is a $\beta^-$-emitter.

10. The complex of claim 9, wherein said $\beta^-$-emitter is $Cu^{67}$.

11. The complex of claim 1, wherein said complex is conjugated to a targeting agent.

12. The complex of claim 11, wherein said targeting agent is an immunological agent, a protein, a polypeptide, a peptide, a nucleic acid or a steroid.

13. The complex of claim 11, wherein said targeting agent is a hormone, a serum protein, a fibrinolytic enzyme or a biological response modifier.

14. A composition comprising a complex of claim 1, optionally conjugated to a targeting agent, and a carrier therefor.

15. A method of synthesizing N,N',N''-trialkyl-cis,cis-1,3,5-triaminocyclohexane, which method comprises:
    (i) derivatizing 1,3,5-cis,cis-triaminocyclohexane to a tris-sulfonamide;
    (ii) removing the sulfonamide proton with a base to generate a tris-anion;
    (iii) quenching the tris-anion with an alkylating agent; and
    (iv) cleaving the sulfonamide group with an acid to generate N,N',N''-trialkyl-cis,cis1,3,5-triaminocyclohexane as a protonated salt.

16. The method of claim 15, which method further comprises:
    (i) adding an equimolar amount of $CuX_2$ in water to the N,N',N''-trialkyl-cis,cis-1,3,5-triaminocyclohexane;
    (ii) neutralizing the compound formed in (i) with base to form a deep-blue solution; and
    (iii) removing hydroxides that form by filtration to yield a solution of the Cu(II) complex of N,N',N''-trialkyl-cis,cis-1,3,5-triaminocyclohexane.

17. A method of cleaving a biological molecule, which method comprises contacting said biological molecule with a complex of claim 1, whereupon said complex cleaves said biological molecule.

18. The method of claim 17, wherein said biological molecule is in vivo and the cleavage of said biological molecule has a therapeutic effect.

19. The method of claim 18, wherein said complex is targeted to an abnormally proliferating cell comprising said biological molecule.

20. The method of claim 19, wherein said abnormally proliferating cell is a cancerous cell and said therapeutic effect is the treatment of cancer.

21. The method of claim 19, wherein said complex is targeted by conjugation to a targeting agent that binds to a molecule on the surface of said abnormally proliferating cell.

22. The method of claim 19, wherein said complex is targeted by encapsulation in a liposome comprising on its surface a targeting agent that binds to a molecule on the surface of said abnormally proliferating cell.

23. The method of claim 21, wherein said targeting agent is an immunological agent.

24. The method of claim 22, wherein the molecule is a sense nucleic acid and the complex encapsulated in a liposome is conjugated to an antisense nucleic acid that binds to the sense nucleic acid, which is expressed in an abnormally proliferating cell but not in a normally proliferating cell or which is expressed in an abnormally proliferating cell at a higher level than in a normally proliferating cell, whereupon expression of said sense nucleic acid is inhibited.

25. The method of claim 19, wherein said complex is targeted by being directly administered to said abnormally proliferating cell.

26. The method of claim 25, wherein said abnormally proliferating cell is a tumor cell and said complex is administered intratumorally or peritumorally.

27. The method of claim 17, wherein the copper is radioactive.

28. The method of claim 24, wherein said antisense nucleic acid further comprises a ribozyme sequence.

29. A method of inhibiting expression of a nucleic acid, which method comprises contacting said nucleic acid with a complex of claim 1, optionally conjugated to a targeting agent, wherein said complex is conjugated to an antisense nucleic acid specific for said nucleic acid, whereupon said antisense nucleic acid binds to said nucleic acid, thereby inhibiting expression of said nucleic acid.

30. The method of claim 29, wherein said antisense nucleic acid further comprises a ribozyme sequence.

31. A method of radiation therapy, which method comprises administering to an animal in need of radiation therapy a therapeutically effective amount of a complex of claim 6, wherein said complex is (i) conjugated to a targeting agent that binds to a molecule on the surface of a cell to be treated with radiation or (ii) encapsulated in a liposome comprising on its surface said targeting agent.

32. A method of imaging, which method comprises (i) administering to an animal an imaging effective amount of a complex of claim 6, wherein said complex is either conjugated to a targeting agent that binds to a molecule on the surface of a cell to be imaged or encapsulated in a liposome comprising on its surface said targeting agent, and (ii) imaging the complex.

33. The method of claim 29, wherein said targeting agent is an immunological agent.

34. A method of tracing a compound in an animal, which method comprises administering to said animal a mixture of said compound and a complex of claim 1 and tracing the location of said complex in said animal, wherein the location of said complex indicates the location of said compound.

35. The method of claim 22, wherein said targeting agent is an immunological agent.

* * * * *